(12) United States Patent  
Hennessy et al.

(10) Patent No.: US 7,488,946 B2  
(45) Date of Patent: Feb. 10, 2009

(54) DIGITAL X-RAY DETECTORS

(75) Inventors: William Andrew Hennessy, Schenectady, NY (US); Bruce Courtney Campbell Amm, Clifton Park, NY (US); Donald Earl Castleberry, Niskayuna, NY (US); Shashishekara Sitharamarao Talya, Houston, TX (US); Virendra Vilas Gaikwad, Bangalore (IN); Shailendra Pramod Joshi, Maharashtra (IN); Habib Vafi, Brookfield, WI (US); Michael John Utschig, Wauwatosa, WI (US)

(73) Assignee: General Electric Company, Niskayuna, NY (US)

( * ) Notice: Subject to any disclaimer, the term of this patent is extended or adjusted under 35 U.S.C. 154(b) by 54 days.

(21) Appl. No.: 11/542,430

(22) Filed: Oct. 3, 2006

(65) Prior Publication Data

US 2008/0078939 A1    Apr. 3, 2008

(51) Int. Cl.  
*G01T 1/24*  (2006.01)

(52) U.S. Cl. .................................. 250/370.09

(58) Field of Classification Search ............ 250/370.09  
See application file for complete search history.

(56) References Cited

U.S. PATENT DOCUMENTS

| | | | |
|---|---|---|---|
| 6,700,126 B2 | 3/2004 | Watanabe | |
| 2006/0071172 A1* | 4/2006 | Ertel et al. | 250/370.11 |
| 2007/0272873 A1* | 11/2007 | Jadrich et al. | 250/370.11 |

* cited by examiner

*Primary Examiner*—Constantine Hannaher  
(74) *Attorney, Agent, or Firm*—Jason K. Klindtworth (57) ABSTRACT

An x-ray detector is provided for use in imaging systems. The x-ray detector includes a detector subsystem configured to output electrical signals in response to reception of x-rays. The x-ray detector also includes a single-piece protective enclosure having at least one opening to receive the detector subsystem.

28 Claims, 5 Drawing Sheets

DIGITAL X-RAY DETECTORS

BACKGROUND

The invention relates generally to x-ray detectors and, more particularly, to the material and construction of structural components of portable digital x-ray detectors.

Imaging systems are utilized for various applications in both medical and non-medical fields. For example, medical imaging systems include general radiological, mammography, x-ray C-arm, tomosynthesis, and computed tomography (CT) imaging systems. These various imaging systems, with their different respective topologies, are used to create images or views of a patient for clinical diagnosis based on the attenuation of radiation (e.g., x-rays) passing through the patient. Alternatively, imaging systems may also be utilized in non-medical applications, such as in industrial quality control or in security screening of passenger luggage, packages, and/or cargo. In such applications, acquired data and/or generated images representing volumes or parts of volumes (e.g., slices) may be used to detect objects, shapes or irregularities which are otherwise hidden from visual inspection and which are of interest to the screener.

Typically, x-ray imaging systems, both medical and non-medical, utilize an x-ray tube to generate the x-rays used in the imaging process. The generated x-rays pass through the imaged object where they are absorbed or attenuated based on the internal structure and composition of the object, creating a matrix or profile of x-ray beams of different strengths. The attenuated x-rays impinge upon an x-ray detector designed to convert the incident x-ray energy into a form usable in image reconstruction. Thus the x-ray profile of attenuated x-rays is sensed and recorded by the x-ray detector. Typically, x-ray detectors are based on film-screen, computed radiography (CR) or digital radiography (DR) technologies. In film-screen detectors, the x-ray image is generated through the chemical development of the photosensitive film after x-ray exposure. In CR detectors, a storage phosphor imaging plate captures the radiographic image. The plate is then transferred to a laser image reader to "release" the latent image from the phosphor and create a digitized image. In DR detectors, a scintillating layer absorbs x-rays and subsequently generates light, which is then detected by a two-dimensional (2D) flat panel array of silicon photo-detectors. Absorption of light in the silicon photo-detectors creates electrical charge. A control system electronically reads out the electrical charge stored in the x-ray detector and uses it to generate a viewable digitized x-ray image.

Digital x-ray detectors typically fabricate the 2D flat panel array of silicon photo-detectors on a glass substrate (imaging panel). Since the imaging panel is fragile, it must therefore be mechanically supported, by some type of panel supports, during use. The panel support also provides stiffness to the overall detector package. Additionally, an external housing or enclosure may be provided to protect the imaging panel. A portion of this external enclosure is generally comprised of a material with low x-ray attenuation characteristics to allow incident x-ray radiation to readily reach the imaging panel.

Typically, the panel supports and the external protective enclosures are composed of heavy machined metal, such as magnesium, so as to provide a high degree of mechanical protection to the flat panel substrate and associated read-out electronic components located within the external housing. Further, the currently available x-ray detectors are based on multi-piece metallic external enclosure assemblies having many weak mechanical seams and screw fasteners both of which are prone to mechanical failure if the detector is dropped or impacted with a rigid object.

Thus, the conventional construction of x-ray detectors results in a relatively heavy and thick x-ray detector that is prone to mechanical failure upon dropping the detector onto a hard surface (i.e. case can dent or break apart). This is particularly problematic for portable x-ray detector designs that should be ideally lightweight while withstanding multiple accidental impact loads. However, the relatively thick and heavy panel support and external enclosure is required to protect the sensitive and fragile imaging components and the readout electronics as these portable detectors are typically used in environments where they can be dropped, impacted with a rigid object, or subjected to a patient load, e.g., placed directly beneath a patient being imaged. For example, the rigid external enclosure prevents the readout electronics from being pressed into the imaging components when subjected to heavy load.

It is therefore desirable to provide an x-ray detector that is lightweight yet mechanically stiff and rugged to withstand heavy impact or support patient loads placed on the detector surface. It is also desirable to provide a stiff support plate onto which the imaging panel is attached so as to protect internal elements of the detector from damage due to heavy impact or patient loads. Additionally, it is desirable to provide a stiff and rugged external enclosure while minimizing or eliminating the weak mechanical attachment points and fasteners required by a multi-piece external enclosure assembly.

BRIEF DESCRIPTION

Briefly in accordance with one aspect of the present technique, an x-ray detector is provided. The x-ray detector includes a detector subsystem configured to output electrical signals in response to reception of x-rays, and a single-piece protective enclosure having at least one opening to receive the detector subsystem.

In accordance with another aspect of the present technique, a portable x-ray detector is provided. The portable x-ray detector includes a detector subsystem configured to output electrical signals in response to reception of x-rays. The detector subsystem includes an imaging panel and associated electronics disposed on a panel support formed of carbon fiber reinforced plastic material. The portable x-ray detector also includes a single-piece protective enclosure formed of carbon fiber reinforced plastic material and having at least one opening to receive the detector subsystem.

In accordance with a further aspect of the present technique, a method is provided for manufacturing an x-ray detector. The method provides for fabricating a single-piece protective enclosure having at least one opening and assembling a detector subsystem configured to output electrical signals in response to reception of x-rays. The detector subsystem includes an imaging panel, a panel support and associated electronics. The method also provides for disposing the detector subsystem within the single-piece protective enclosure via the at least one opening.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is generally directed to portable digital x-ray detectors. Generally, these detectors may be used in a variety of imaging systems, such as for medical imaging, industrial imaging, and baggage or package screening. Though the present discussion provides examples in a medical imaging context, one of ordinary skill in the art will readily comprehend that the application of these detectors in other contexts, such as for industrial imaging, security screening, and/or baggage or package inspection, is well within the scope of the present technique.

The present invention will be described with respect to a digital flat panel, solid-state, indirect detection, portable x-ray detector for use with a mobile x-ray imaging system. However, the present invention is equivalently applicable with other types of x-ray detectors including direct detection digital detectors. Additionally, the present invention may be used with stationary or fixed room x-ray imaging systems. Further, the present application makes reference to an imaging "subject" as well as an imaging "object". These terms are not mutually exclusive and, as such, use of the terms is interchangeable and is not intended to limit the scope of the appending claims.

Figure 1:
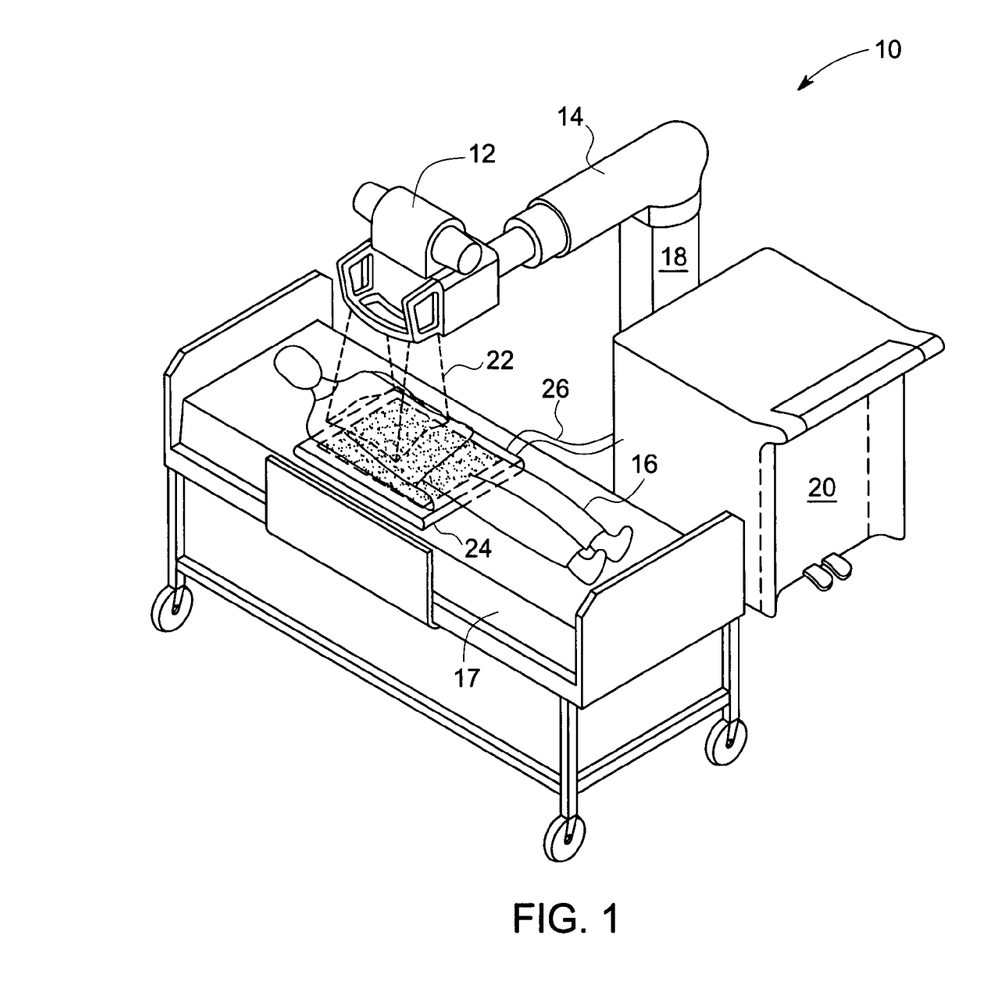
FIG. 1 depicts an exemplary mobile x-ray imaging system using a portable digital x-ray detectors in accordance with one aspect of the present technique.

Referring now to FIG. 1, an exemplary mobile x-ray imaging system 10 employing a portable x-ray detector is illustrated. In the illustrated embodiment, the mobile x-ray imaging system 10 includes a radiation source 12, such as an x-ray source 12 mounted or otherwise secured to an end of horizontal arm 14. The arm 14 allows the x-ray source 12 to be variably positioned above a subject 16, resting on a patient table or bed 17, in such a manner so as to optimize irradiation of a particular area of interest. The x-ray source 12 is typically mounted through a gimbal-type arrangement (not shown) in column 18. In this regard, the x-ray source 12 may be rotated vertically from a rest or park position on the mobile x-ray unit base 20 to the appropriate position above the subject 16 in order to take an x-ray exposure of the subject 16. The rotational movement of column 18 is typically limited to a value of 360 degrees or less to prevent entanglement of high voltage cables (not shown) used to provide electrical power to the x-ray source 12. The cables may be connected to a utility line source (not shown) or a battery (not shown) in the base 20 to energize the x-ray source 12 as well as other electronic components of the system 10.

The x-ray source 12 projects a fan beam of radiation 22 toward the subject 16 to be imaged. One skilled in the art will appreciate that medical patients as well as luggage, packages, and the like may be non-invasively inspected using the exemplary x-ray imaging system 10. A portable x-ray detector 24 placed beneath the subject 16 acquires the attenuated radiation and generates a detector output signal. The detector output signal may then be transmitted to the mobile imaging system 10 over a wired or a wireless link 26. One skilled in the art will appreciate that the system 10 may be equipped with or connectable to a display unit (not shown) for the display of images captured from the imaging subject 16.

Figure 2:
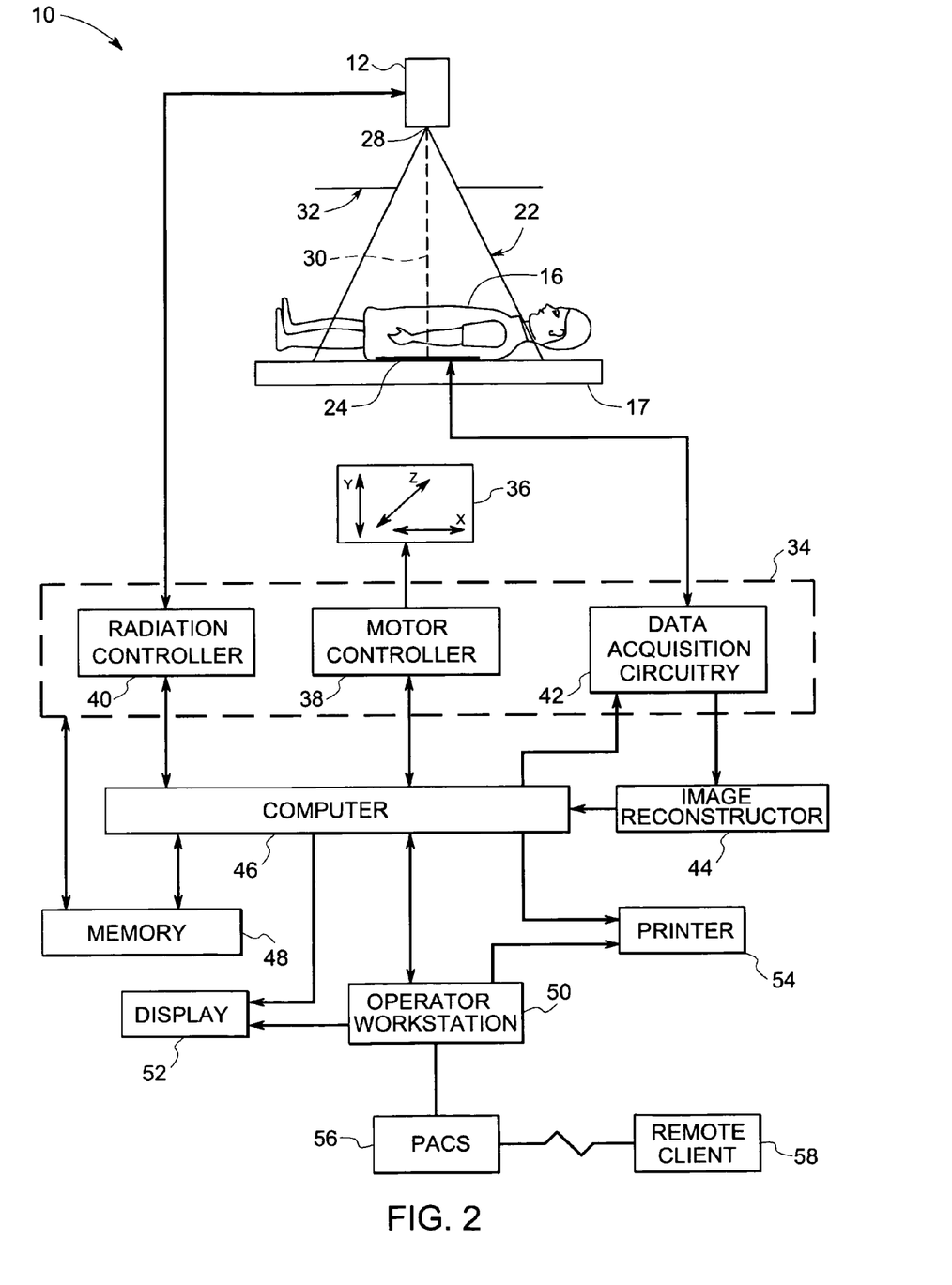
FIG. 2 depicts a schematic block diagram of the exemplary x-ray imaging system of FIG. 1.

A schematic of the x-ray imaging system 10 of FIG. 1 is shown in FIG. 2. As described above, the system 10 includes the x-ray source 12 designed to project the fan bean of radiation 22 from focal spot 28 along axis 30 toward the subject 16 to be imaged. The radiation 22 passes through the subject 16, which provides the attenuation, and resulting attenuated portion of the radiation impacts the detector array 24. It should be noted that portions of the x-ray beam 22 may extend beyond the boundary of the patient 16 and may impact detector array 24 without being attenuated by the patient 16. In the embodiments discussed herein, a flat panel digital detector may be employed to detect the intensity of radiation 22 transmitted through or around the subject 16 and to generate a detector output signal in response to the detected radiation. A collimator 32 may be positioned adjacent to the x-ray source 12. The collimator typically defines the size and shape of the x-ray fan beam 22 that pass into a region in which a subject 16, such as a human patient, is positioned and may therefore control the scope of irradiation.

The digital detector 24 is generally formed by a plurality of detector elements, which detect the x-rays 22 that pass through or around the subject 16. For example, the detector 24 may include multiple rows and/or columns of detector elements arranged in a two-dimensional array. Each detector element, when impacted by an x-ray flux, produces an electrical signal proportional to the absorbed x-ray flux at the position of the individual detector element in detector 24. These signals are acquired and processed to reconstruct an image of the features within the subject, as described below.

The radiation source 12 is controlled by a system controller 34, which furnishes power, focal spot location, control signals and so forth for imaging sequences. Moreover, the detector 24 is coupled to the system controller 34, which controls the acquisition of the signals generated in the detector 24. The system controller 34 may also execute various signal processing and filtration functions, such as for initial adjustment of dynamic ranges, interleaving of digital image data, and so forth. In general, system controller 34 commands operation of the imaging system 10 to execute examination protocols and to process acquired data. In the present context, system controller 34 may also include signal processing circuitry, typically based upon a general purpose or application-specific digital computer, and associated memory circuitry. The associated memory circuitry may store programs and routines executed by the computer, configuration parameters, image data, and so forth. For example, the associated memory circuitry may store programs or routines for reconstructing image from the detector output signal.

In the embodiment illustrated in FIG. 2, the system controller 34 may control the movement of a motion subsystem 36 via a motor controller 38. In the depicted imaging system 10, the motion subsystem 36 may move the x-ray source 12, the collimator 32, and/or the detector 24 in one or more directions in space with respect to the patient 16. It should be noted that the motion subsystem 36 might include a support structure, such as a C-arm or other movable arm, on which the source 12 and/or the detector 24 may be disposed. The motion subsystem 36 may further enable the patient 16, or more specifically the patient table 17, to be displaced with respect to the source 12 and the detector 24 to generate images of particular areas of the patient 16.

As will be appreciated by those skilled in the art, the source 12 of radiation may be controlled by a radiation controller 40 disposed within the system controller 34. The radiation controller 40 may be configured to provide power and timing signals to the radiation source 12. In addition, the radiation controller 40 may be configured to provide focal spot location, for example, emission point activation, if the source 12 is a distributed source comprising discrete electron emitters.

Further, the system controller 34 may comprise data acquisition circuitry 42. In this exemplary embodiment, the detector 24 is coupled to the system controller 34, and more particularly to the data acquisition circuitry 42. The data acquisition circuitry 42 receives data collected by readout electronics of the detector 24. In particular, the data acquisition circuitry 42 typically receives sampled analog signals from the detector 24 and converts the data to digital signals for subsequent processing by an image reconstructor 44 and/or a computer 46.

The computer or processor 46 is typically coupled to the system controller 34 and may include a microprocessor, digital signal processor, microcontroller, as well as other devices designed to carry out logic and processing operations. The data collected by the data acquisition circuitry 42 may be transmitted to the image reconstructor 44 and/or the computer 46 for subsequent processing and reconstruction. For example, the data collected from the detector 24 may undergo pre-processing and calibration at the data acquisition circuitry 42, the image reconstructor 44, and/or the computer 46 to condition the data to represent the line integrals of the attenuation coefficients of the scanned objects. The processed data may then be reordered, filtered, and backprojected to formulate an image of the scanned area. Although a typical filtered back-projection reconstruction algorithm is described in the present aspect, it should be noted that any suitable reconstruction algorithm may be employed, including statistical reconstruction approaches. Once reconstructed, the image produced by the imaging system 10 reveals an internal region of interest of the patient 16 which may be used for diagnosis, evaluation, and so forth.

The computer 46 may comprise or communicate with a memory 48 that can store data processed by the computer 46 or data to be processed by the computer 46. It should be understood that any type of computer accessible memory device capable of storing the desired amount of data and/or code may be utilized by such an exemplary system 10. Moreover, the memory 48 may comprise one or more memory devices, such as magnetic or optical devices, of similar or different types, which may be local and/or remote to the system 10. The memory 48 may store data, processing parameters, and/or computer programs comprising one or more routines for performing the reconstruction processes. Furthermore, memory 48 may be coupled directly to system controller 34 to facilitate the storage of acquired data.

The computer 46 may also be adapted to control features enabled by the system controller 34, i.e., scanning operations and data acquisition. Furthermore, the computer 46 may be configured to receive commands and scanning parameters from an operator via an operator workstation 50 which may be equipped with a keyboard and/or other input devices. An operator may thereby control the system 10 via the operator workstation 50. Thus, the operator may observe the reconstructed image and other data relevant to the system from operator workstation 50, initiate imaging, and so forth.

A display 52 coupled to the operator workstation 50 may be utilized to observe the reconstructed image. Additionally, the scanned image may be printed by a printer 54 coupled to the operator workstation 50. The display 52 and the printer 54 may also be connected to the computer 46, either directly or via the operator workstation 50. Further, the operator workstation 50 may also be coupled to a picture archiving and communications system (PACS) 56. It should be noted that PACS 56 might be coupled to a remote system 58, such as a radiology department information system (RIS), hospital information system (HIS) or to an internal or external network, so that others at different locations may gain access to the image data.

One or more operator workstations 50 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The exemplary imaging system 10, as well as other imaging systems based on radiation detection, employs a detector 24, such as a flat panel, digital x-ray detector. A perspective view of such an exemplary flat panel, digital x-ray detector 60 is provided in FIG. 3. The exemplary flat panel, digital x-ray detector 60 includes a detector subsystem (not shown) for generating electrical signals in response to reception of incident x-rays. In accordance with aspects of the present technique, a single-piece protective housing 62 provides an external enclosure to the detector subsystem, so as to protect the fragile detector components from damage when exposed to an external load or an impact. As will be appreciated by one skilled in the art, the single-piece protective enclosure 62 may be a continuous structure and may be substantially devoid of any discontinuities. In one embodiment, the single-piece protective enclosure may be a 4-5 sided structure in a sleeve like configuration having at least one opening to allow for the insertion of the detector subsystem. It should be noted that, the individual sides or edges of the single-piece sleeve need not be flat but may be rounded, curved, contoured, or shaped to improve detector ruggedness and ease of use. The single-piece protective enclosure 62 may be formed of materials such as a metal, a metal alloy, a plastic, a composite material, or a combination of the above. It should be noted that the material must have low x-ray attenuation characteristics. In one embodiment, the protective enclosure 62 may be formed of a lightweight, durable composite material such as a carbon fiber reinforced plastic material. Additionally, as will be appreciated by one skilled in the art, the single-piece protective enclosure 62 may be designed to be substantially rigid with minimal deflection when subjected to an external load.

Figure 3:
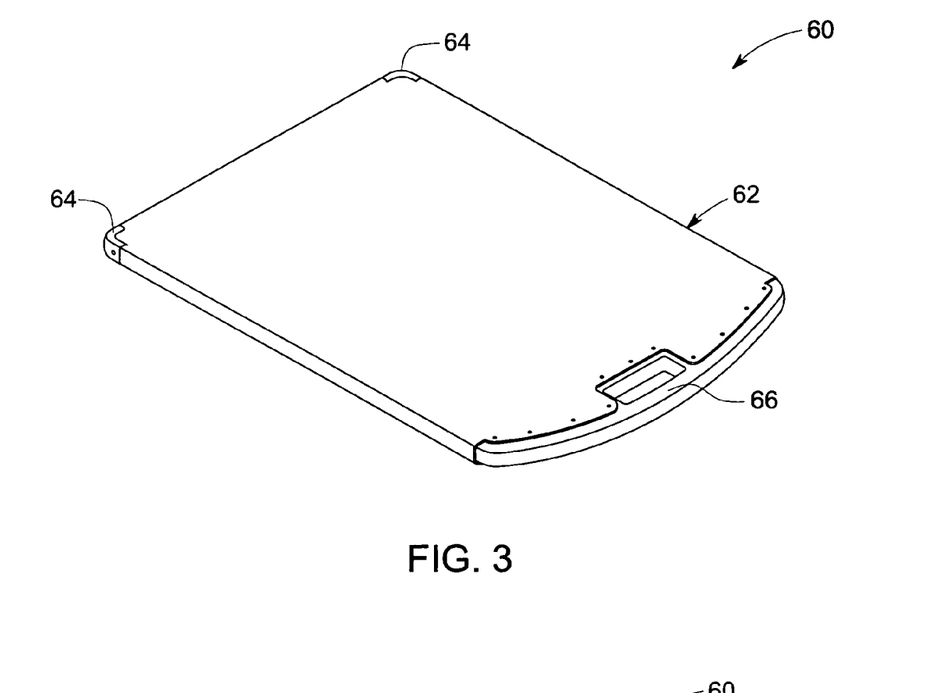
FIG. 3 depicts a perspective view of a portable flat panel digital x-ray detector in accordance with one aspect of the present technique.
Figure 6:
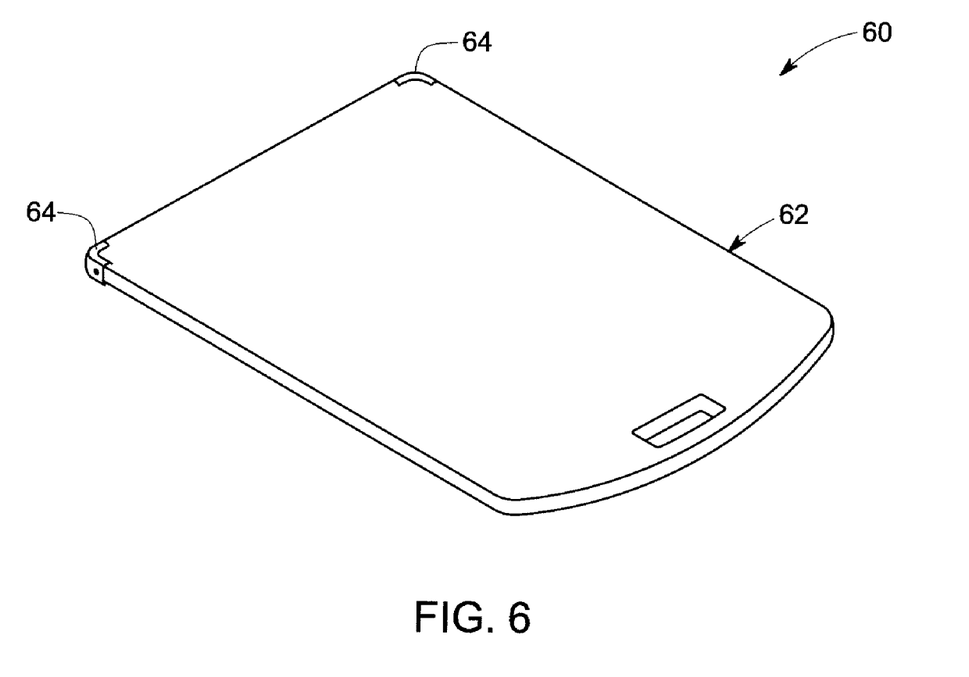
FIG. 6 depicts a perspective view of a portable flat panel digital x-ray detector in accordance with another aspect of the present technique.

One or more corner or edge caps 64 may be provided at respective corners, edges, or a portion of respective edges of the single-piece protective enclosure 62. It should be noted that the one or more corner or edge caps 64 may be formed of an impact resistant, energy absorbent material such as nylon, polyethylene, ultra high molecular weight polyethylene (UHMW-PE), delrin, or polycarbonate. UHMW polyethylene is a linear polymer with a molecular weight in the range of 3,100,000 to 6,000,000. Further, a handle 66 may be mechanically coupled to the single-piece protective enclosure 62 to support the portability of the detector 60. This handle may be a separate component, which is attached to the single-piece protective enclosure 62. Again, it should be noted that the handle 66 may be formed of an impact resistant, energy absorbent material such as a high molecular weight polyethylene. Alternatively, as will be appreciated by one skilled in the art, in certain embodiments, the handle 66 may be a continuous extension of the single-piece protective enclosure 62, as illustrated in FIG. 6. In other words, the handle 66 may be formed integrally with the single-piece protective enclosure, thereby eliminating or minimizing the mechanical attachment points between the handle 66 and the protective enclosure 62. A removable edge cap may be provided in such embodiments to allow for the insertion of the detector subsystem into the single-piece protective enclosure 62.

As shown, the detector 24 may be constructed without a fixed tether. Alternatively, the detector may be connected to a tether (not shown) that is used to connect the detector readout electronics to the data acquisition system of the scanner when in use. When not in use, the detector may be easily detached from tether and stored remotely from the imaging system. As such, detector may be transported to and from multiple scan stations remote from one another. This is particularly advantageous for emergency rooms and other triage facilities. As will be appreciated by one skilled in the art, the portability and detachability of the detector further enhances the mobility of a mobile x-ray imaging system, such as that shown in FIG. 1.

Figure 4:
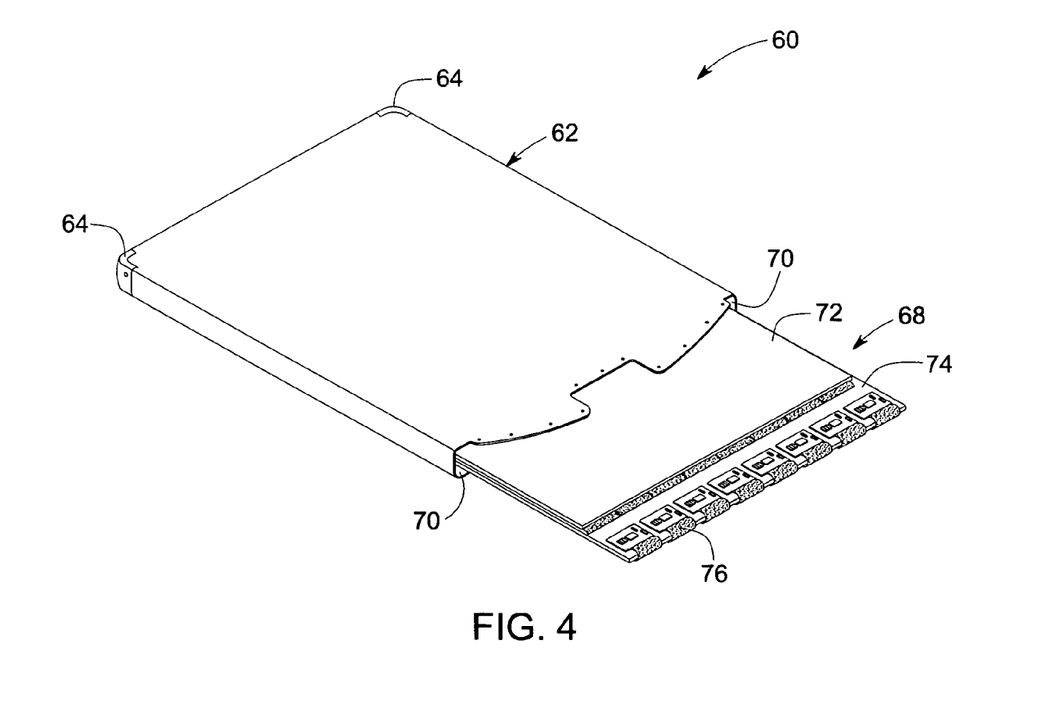
FIG. 4 depicts a digital detector subsystem disposed within the single-piece protective enclosure through an opening in the portable flat panel digital x-ray detector of FIG. 3.

FIG. 4 illustrates the detector subsystem 68 of the portable flat panel digital x-ray detector 60 disposed within the single-piece protective enclosure 62 through an opening 70. As will be appreciated by one skilled in the art, the detector subsystem 68 generally includes an imaging panel 72, a panel support 74, and associated read-out electronics 76. The imaging panel 72 generally includes a scintillator layer for converting incident x-rays to visible light. The scintillator layer, which may be fabricated from Cesium Iodide (CsI) or other scintillating materials, is designed to emit light proportional to the energy and the amount of the x-rays absorbed. As such, light emissions will be higher in those regions of the scintillator layer where either more x-rays were received or the energy level of the received x-rays was higher. Since the composition of the subject will attenuate the x-rays projected by the x-ray source to varying degrees, the energy level and the amount of the x-rays impinging upon the scintillator layer will not be uniform across the scintillator layer. This variation in light emission will be used to generate contrast in the reconstructed image.

The light emitted by the scintillator layer is detected by a photosensitive layer on the 2D flat panel substrate. The photosensitive layer includes an array of photosensitive elements or detector elements to store electrical charge in proportion to the quantity of incident light absorbed by each detector elements. Generally, each detector element has a light sensitive region and a region comprising of electronics to control the storage and output of electrical charge from that detector element. The light sensitive region is typically composed of a photodiode, which absorbs light and subsequently creates and stores electronic charge. After exposure, the electrical charge in each detector element is read out using logic-controlled electronics 76.

Each detector element is generally controlled using a transistor-based switch. In this regard, the source of the transistor is connected to the photodiode, the drain of the transistor is connected to a readout line, and the gate of the transistor is connected to a scan control interface disposed on the electronics 76 in the detector 60. When negative voltage is applied to the gate, the switch is driven to an OFF state, thereby preventing conduction between the source and the drain. Conversely, when a positive voltage is applied to the gate, the switch is turned ON, thereby allowing charge stored in the photodiode to pass from the source to the drain and onto the readout line. Each detector element of the detector array is constructed with a respective transistor and is controlled in a manner consistent with that described below.

Specifically, during exposure to x-rays, negative voltage is applied to all gate lines resulting in all the transistor switches being driven to or placed in an OFF state. As a result, any charge accumulated during exposure is stored in the photodiode of each detector element. During read out, positive voltage is sequentially applied to each gate line, one gate line at a time. That is, the detector is an X-Y matrix of detector elements and all of the gates of the transistors in a line are connected together so that turning ON one gate line simultaneously reads out all the detector elements in that line. In this regard, only one detector line is read out at a time. A multiplexer (not shown) may also be used to support read out of the detector elements in a raster fashion. An advantage of sequentially reading out each detector element individually is that the charge from one detector element does not pass through any other detector elements. The output of each detector element is then input to an output circuit (e.g., a digitizer) that digitizes the acquired signals for subsequent image reconstruction on a per pixel basis. Each pixel of the reconstructed image corresponds to a single detector element of the detector array.

The imaging panel 72 is supported by a thin and lightweight panel support 74. The readout electronics and other electronics 76 are disposed on the panel support 74 on the side opposite from the imaging panel 72. That is, the panel support 74 mechanically isolates the imaging components of the imaging panel 72 from the readout electronics 76.

Generally, the panel support 74 may be formed of a metal, a metal alloy, a plastic, a composite material, or a combination of the above material. In one embodiment, the panel support 74 may be substantially formed of a carbon fiber reinforced plastic material. In another embodiment, the panel support 74 may be substantially formed of composite materials in combination with foam cores in a laminated sandwich construction so as to provide a lightweight yet stiff assembly to serve as the panel support. The construction of panel support 74 from the composite materials alone or composite materials in combination with foam cores reduces weight while providing greater mechanical stiffness and improved energy absorption capability.

As will be appreciated by one skilled in the art, the composite materials are typically combinations of a reinforcement and a matrix. The matrix material, typically a resin or epoxy, surrounds and supports the reinforcement material. The reinforcement materials, typically organic or inorganic fibers or particles, are bound together by the composite matrix. For fiber reinforcements, the direction the individual fibers may be oriented to control the rigidity and the strength of the composite. Further, the composite may be formed of several individual layers with the orientation or alignment of the reinforcement layers varying through the thickness of composite. The construction may be a laminate type construction (containing layers of reinforcements only) or a sandwich type construction (where a soft core is inserted between two sets of reinforcement layers). The resins used could be thermosets or thermoplastics. In sandwich type construction, the soft core can result in additional weight reduction and could have metal or non-metallic pins to enhance the energy absorption capability. Also, the layers of the composite could use multiple materials (Carbon, Kevlar, Aluminum foil etc.) in different forms (particles, fibers, fabric, thin foils etc). In one embodiment, the composite material for the portable x-ray detector 60 may be configured from carbon fibers or epoxy resins in a layered construction with a foam core.

Figure 5:
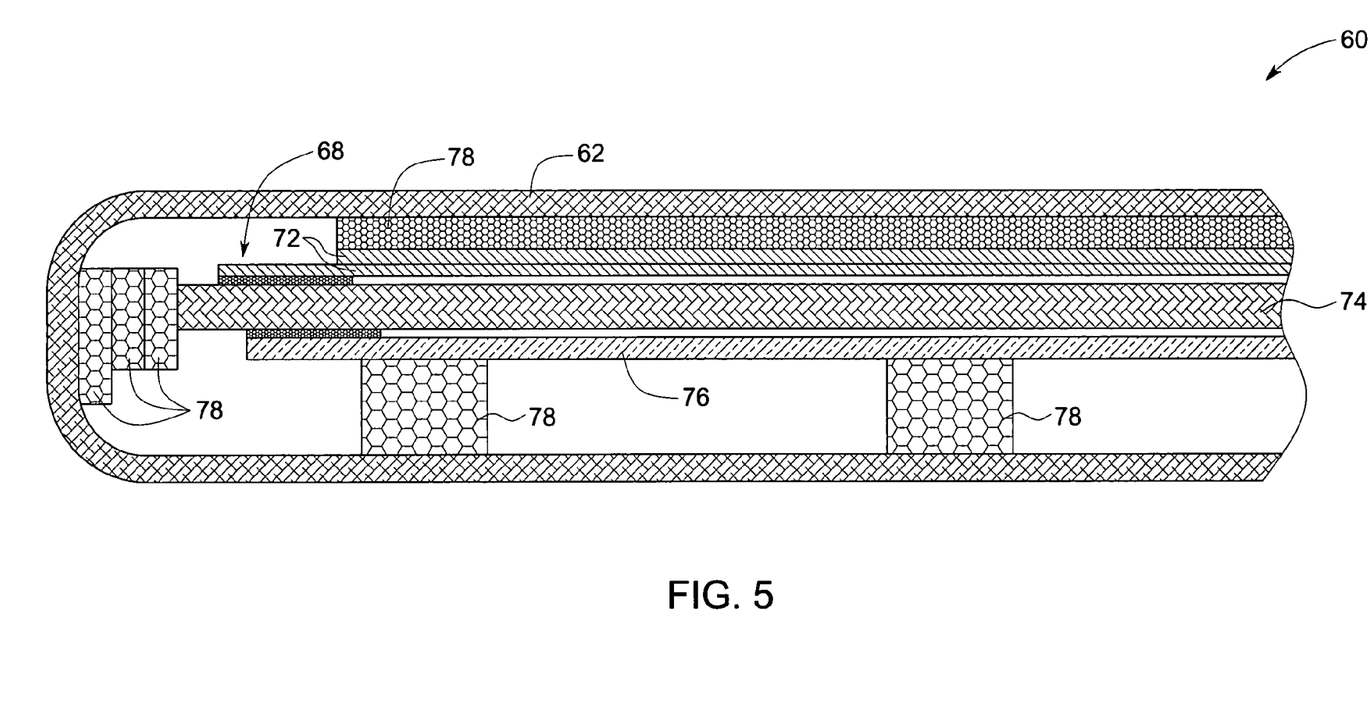
FIG. 5 depicts a cross-sectional view of the portable flat panel digital x-ray detector of FIG. 3.

Referring now to FIG. 5, a cross-sectional view of the portable flat panel digital x-ray detector 60 is illustrated in accordance with aspects of the present technique. As depicted, one or more layers 78 of compressible material may be disposed on one or more portions of the inner surface of the single-piece protective enclosure 62, in accordance with the aspects of the present technique, to hold the detector subsystem 68 such that the detector subsystem 68 is suspended (free floating) within the single-piece protective enclosure 62 and not rigidly attached to the external protective enclosure 62. As will be appreciated by one skilled in the art, in one embodiment, the compressible material may be impact absorbing materials such as rubber, foam, elastomer, foam rubber, or other elastic materials.

Additionally, the single piece protective enclosure 62 may be constructed with bumpers, foam inserts, layers of impact absorbing material, and the like to inhibit fracturing of the detector components when dropped or subjected to a load. As described above, the x-ray detector is designed to withstand relatively high-energy impacts, stresses, and strains such that the relatively sensitive components, such as imaging panel and associated electronics, are not damaged when the detector is dropped or subjected to external load. In one embodiment, the x-ray detector 60 includes two layers of impact-absorbing material sealed against or otherwise placed under the top and bottom surfaces of the single piece protective enclosure 62. Further, as will be appreciated by one skilled in the art, the detector 60 may include multiple layers of impact absorbing materials interstitially disposed between the detector components.

It should be noted that the impact-absorbing material is designed not to attenuate radiation so as not to interfere with data acquisition. As will be appreciated by one skilled in the art, the impact-absorbing material is an elastic material configured to absorb the shock and vibrations placed on the detector when dropped and to deflect the force placed on the detector when stepped upon or otherwise subjected to a load, e.g. patient weight. The elastic material may be rubber, foam, foam rubber, or other plastic and is designed to deflect and absorb stresses and strains on the detector. As such, when the detector is stepped upon or dropped, the internal components of the detector do not fracture or are otherwise damaged. One skilled in the art will appreciate that the thickness, density and composition of the impact-absorbing material may be variably selected to define the limits by which the detector may be subjected to a load or dropped without damage to the detector components.

Further, the two impact absorbing layers may have similar or dissimilar thicknesses, and may be composed of similar or dissimilar impact absorbing material(s). For example, the top layer may be designed to be more absorbent and deflective than the bottom layer and may therefore be thicker than the bottom layer or may be formed from material with improved absorption and deflective characteristics. In one embodiment, the top layer may be formed of foam having pronounced elastic properties whereas the bottom layer may be formed of polyurethane, PVC, or other material with less pronounced elastic characteristics.

The portable x-ray detector described in various embodiments discussed above is lightweight yet mechanically stiff and rugged and has improved energy absorption capability. The structural load bearing components (the protective enclosure and the panel support) of the portable x-ray detector are made up of a composite material. The composite material offer high mechanical rigidity and strength while simultaneously making the construction lightweight. As will be appreciated by one skilled in the art, the low density of the composite material used helps reduce the weight while the high modulus and strength of the carbon fiber composite helps to make the construction rigid and strong.

The sleeve design (open on at least 1 end for insertion of detector subsystem) of the protective enclosure provides mechanical ruggedness since fasteners are no longer required to hold the faces and sides of the external enclosure together. Additionally, the design allows for the fabrication with either composites or plastics and therefore reduces weight and improves mechanical toughness. As will be appreciated by one skilled in the art, the single-piece design of the external enclosure is more rugged since multi-piece assembly can fail during mechanical impact. Moreover, the use of thermoplastic based epoxy or rubber toughened epoxy in composite construction improves energy absorption.

Further, the new packaging design for the portable x-ray detector, described in various embodiments discussed above, isolates the fragile detector subsystem (imaging panel and readout electronics) from the external protective enclosure by employing shock absorbing elastomeric foam pieces on all sides. As will be appreciated by one skilled in the art, isolating of the detector subsystem from the external protective enclosure protects the detector subsystem from external shocks and stresses occurring as a result of being dropped or banged against hard objects accidentally.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An x-ray detector, comprising:
   a detector subsystem configured to output electrical signals in response to reception of x-rays; and
   a single-piece protective enclosure having at least one opening to receive the detector subsystem.

2. The x-ray detector of claim 1, wherein at least a portion of the single-piece protective enclosure comprises a material having low x-ray attenuation characteristics.

3. The x-ray detector of claim 1, wherein the single-piece protective enclosure comprises at least one of a metal, a metal alloy, a plastic, a composite material, or a combination thereof.

4. The x-ray detector of claim 1, wherein the single-piece protective enclosure comprises a carbon fiber reinforced plastic material.

5. The x-ray detector of claim 1, wherein the detector subsystem further comprises an imaging panel, a panel support and associated electronics.

6. The x-ray detector of claim 5, wherein the panel support comprises at least one of a metal, a metal alloy, a plastic, a composite material, a composite material in combination with foam cores, or a combination thereof.

7. The x-ray detector of claim 5, wherein the panel support comprises a carbon fiber reinforced plastic material or a carbon fiber reinforced plastic material in combination with foam cores.

8. The x-ray detector of claim 1, further comprising one or more corner or edge caps disposed on respective corners, edges, or a portion of respective edges of the single-piece protective enclosure.

9. The x-ray detector of claim 8, wherein the one or more corner or edge caps comprises an impact resistant, energy absorbent material.

10. The x-ray detector of claim 8, wherein the one or more corner or edge caps comprises a high molecular weight polyethylene.

11. The x-ray detector of claim 1, further comprising a handle mechanically coupled to the single-piece protective enclosure.

12. The x-ray detector of claim 11, wherein the handle comprises an impact resistant, energy absorbent material.

13. The x-ray detector of claim 11, wherein the handle comprises a high molecular weight polyethylene.

14. The x-ray detector of claim 1, wherein the single-piece protective enclosure extends to form a handle.

15. The x-ray detector of claim 1, further comprising one or more layers of compressible material disposed on one or more portions of the inner surface of the single-piece protective enclosure to hold the detector subsystem.

16. The x-ray detector of claim 15, wherein the compressible material comprises a rubber, an elastomer, or a foam rubber.

17. The x-ray detector of claim 1, further comprising one or more layers of impact absorbing material disposed between different components of the x-ray detector.

18. The x-ray detector of claim 17, wherein the impact absorbing material comprises a rubber, a foam rubber, a polyurethane, or a PVC.

19. A portable x-ray detector, comprising:
   a detector subsystem configured to output electrical signals in response to reception of x-rays, the detector subsystem comprising an imaging panel and associated electronics disposed on a panel support formed of carbon fiber reinforced plastic material;
   a single-piece protective enclosure formed of carbon fiber reinforced plastic material and having at least one opening to receive the detector subsystem.

20. The portable x-ray detector of claim 19, further comprising one or more corner or edge caps formed of impact resistant, energy absorbent material and disposed on respective corners, edges, or a portion of respective edges of the single-piece protective enclosure.

21. The portable x-ray detector of claim 19, further comprising a handle formed of impact resistant, energy absorbent material and mechanically coupled to the single-piece protective enclosure to carry the portable x-ray detector.

22. The portable x-ray detector of claim 19, further comprising one or more layers of compressible material disposed on one or more portions of the inner surface of the single-piece protective enclosure to hold the detector subsystem.

23. The portable x-ray detector of claim 19, further comprising one or more layers of impact absorbing material disposed between different components of the portable x-ray detector.

24. A method of manufacturing an x-ray detector, the method comprising:
   fabricating a single-piece protective enclosure having at least one opening;
   assembling a detector subsystem configured to output electrical signals in response to reception of x-rays, the detector subsystem comprising an imaging panel, a panel support and associated electronics; and
   disposing the detector subsystem within the single-piece protective enclosure via the at least one opening.

25. The method of claim 24, further comprising disposing one or more corner or edge caps on respective corners, edges, or a portion of respective edges of the single-piece protective enclosure.

26. The method of claim 24, further comprising mechanically coupling a handle to the single-piece protective enclosure.

27. The method of claim 24, further comprising disposing one or more layers of compressible material on one or more portions of the inner surface of the single-piece protective enclosure to hold the detector subsystem.

28. The method of claim 24, further comprising disposing one or more layers of impact absorbing material between different components of the x-ray detector.

* * * * *